United States Patent [19]

Taylor, Jr. et al.

[11] Patent Number: 5,066,654
[45] Date of Patent: Nov. 19, 1991

[54] 2-ARYL-3-HETEROCYCLICMETHYL-3H-IMIDAZO[4,5-B]PYRIDINES AS ANXIOLYTICS AND ANTICONVULSANTS

[75] Inventors: Chandler R. Taylor, Jr., Mechanicsville; Meredith Moses, Glen Allen, both of Va.

[73] Assignee: A. H. Robins Company, Incorporated, Richmond, Va.

[21] Appl. No.: 601,967

[22] Filed: Oct. 22, 1990

[51] Int. Cl.$^5$ ............... A61K 31/505; A61K 31/435; C07D 471/04
[52] U.S. Cl. ................... 514/256; 514/269; 514/300; 544/298; 544/319; 544/322; 544/328; 544/333; 546/118
[58] Field of Search ........ 514/256, 269, 300; 544/298, 319, 322, 328, 333; 546/118

[56] References Cited

U.S. PATENT DOCUMENTS

| | | | |
|---|---|---|---|
| 3,985,891 | 10/1976 | Kutter et al. | 546/118 |
| 4,327,100 | 4/1982 | Austel et al. | 546/118 |
| 4,353,909 | 10/1982 | Diederen et al. | 546/118 |
| 4,772,600 | 9/1988 | Tomczuk et al. | 514/234.2 |
| 4,824,951 | 4/1989 | Tomczuk et al. | 546/118 |
| 4,873,251 | 10/1989 | Tomczuk et al. | 514/303 |

OTHER PUBLICATIONS

Chem. Abstracts, vol. 84, 59315u (1975).

Primary Examiner—Bernard Dentz
Attorney, Agent, or Firm—Richard K. Jackson

[57] ABSTRACT

There are disclosed compounds of the formula

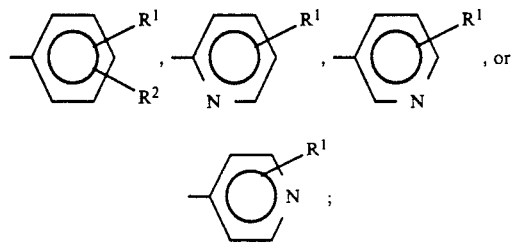

wherein
Ar is

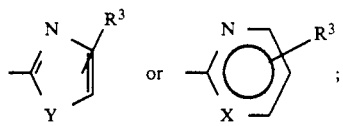

Het is $R^1$, $R^2$, and $R^3$ are each, independently, hydrogen, alkyl, aralkyl, alkoxy, carbalkoxy, trifluoromethyl, halo, cyano, or nitro;
$R^4$ is hydrogen, alkyl, aralkyl, alkoxy, carbalkoxy, halo, or trifluoromethyl;
Y is NH, O, or S;
X is CH, or N;
or a pharmaceutically acceptable salt thereof, which, by virtue of their ability to bind to the benzodiazepine receptor, and prevent electrically or chemically induced seizures are useful as anxiolytic and anticonvulsant agents.

19 Claims, No Drawings

2-ARYL-3-HETEROCYCLICMETHYL-3H-IMIDAZO[4,5-B]PYRIDINES AS ANXIOLYTICS AND ANTICONVULSANTS

BACKGROUND OF THE INVENTION

The present invention relates to certain novel imidazo[4,5-b]pyridines useful as anxiolytic and anticonvulsant agents, by virtue of their ability to bind to the benzodiazepine receptors and inhibit electrically or chemically induced seizures.

The preparation of fused imidazoheterocycles containing an aryl substituent on the 2-carbon of the imidazole ring have been disclosed in U.S. Pat. Nos. 4,772,600, 4,824,951 and 4,873,251 as methods of treating muscle spasticity and anxiety and preventing seizures.

The preparation of 2-aryl-imidazo[4,5-b]pyridines devoid of substitution on the imidazo nitrogen has been disclosed by Garmaise, D. L. and Komlossy in J. Org. Chem. 29(1), 3404–5 (1964).

U.S. Pat. Nos. 3,985,891, 4,327,100 and 4,353,909 disclose 2-phenylimidazopyridines which are taught to be cardiotonics and blood pressure altering drugs.

2-Aryl-imidazo[4,5-b]pyridines with an N-methyl imidazo-substituent were disclosed in Montash Chem. (1975), 106(5), pp 1059–69 (C.A. 84,59315) as having no significant biological activity as compared to 2-(α-hydroxybenzyl)benzimidazole.

DESCRIPTION OF THE INVENTION

The invention provides compounds of the formula

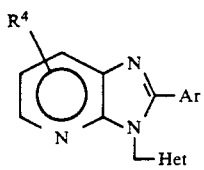

wherein
Ar is

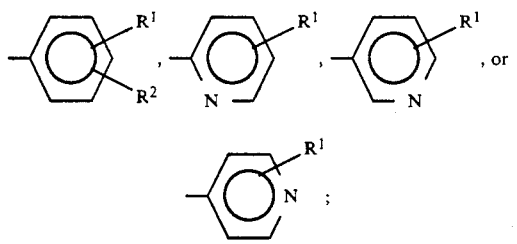

Het is

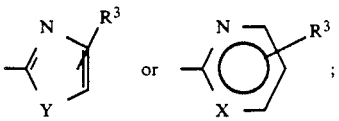

$R^1$, $R^2$, and $R^3$ are each, independently, hydrogen, alkyl of 1–6 carbon atoms, aralkyl of 7–10 carbon atoms, alkoxy of 1–6 carbon atoms, carbalkoxy of 2–7 carbon atoms, trifluoromethyl, halo, cyano, or nitro;

$R^4$ is hydrogen, alkyl of 1–6 carbon atoms, aralkyl of 7–10 carbon atoms, alkoxy of 1–6 carbon atoms, carbalkoxy of 2–7 carbon atoms, halo, or trifluoromethyl;

Y is NH, O, or S;

X is CH, or N;

or a pharmaceutically acceptable salt thereof.

Based on the above-described genus of compounds the following structures represent preferred compounds from the standpoint of production economics and activity profile wherein $R^1$, $R^2$, $R^3$, $R^4$, and X as are defined above.

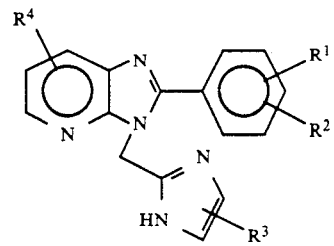

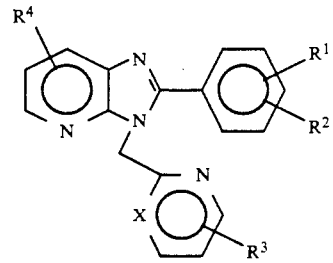

The pharmaceutically acceptable salts may be formed with organic and inorganic acids such as hydrochloric, hydrobromic, phosphoric, sulfuric, sulfonic, nitric, methylsulfonic, acetic, maleic, succinic, fumaric, tartaric, citric, salicyclic, lactic, naphthalenesulfonic acid, and the like.

The compounds of the invention can be prepared by the following route starting with an appropriately substituted 2-chloro-3-nitropyridine

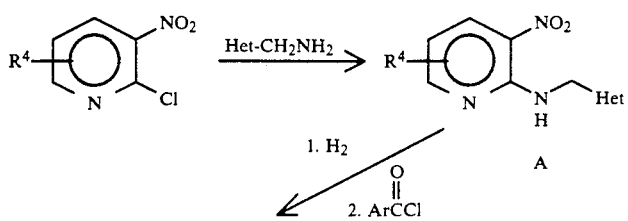

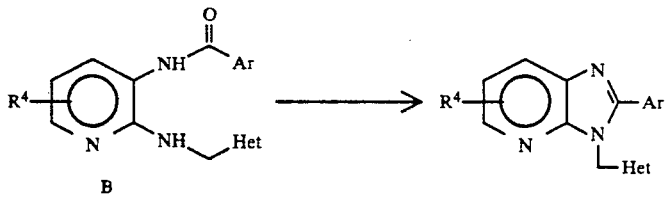

which is reacted with a 2-(aminomethyl) heterocycle to give intermediate A. The nitro substituent is reduced by catalytic hydrogenation over palladium or platinum. The resulting amine is acylated with an appropriately substituted aroyl chloride to give intermediate B. Ring closure to give the final product can be accomplished by heating intermediate B in an inert solvent under acidic, basic, or neutral conditions.

Both of the intermediates A and B can be isolated and characterized, although the synthesis can be accomplished without isolation of either intermediate.

Alternatively, the sequence can be reversed so that the reduction/acylation step is carried out first followed by reaction with the 2-(aminomethyl) heterocycle, and subsequent ring closure to give the final product.

The starting materials used in the above outlined preparative sequences are all available commercially or can be prepared by conventional methods disclosed in the literature.

The anxiolytic and anticonvulsant activities of representative compounds of this invention were evaluated using standard pharmacological test procedures. A brief description of these procedures and results are provided below.

Anxiolytic activity was evaluated in vitro according to the method of Chiu et al. [Mol. Pharmacol. 21, 57 (1982)] by determining the $IC_{50}$ for the inhibition of [$^3$H]-flunitrazepam binding to the benzodiazepine receptor.

Anxiolytic activity also was evaluated in vivo in an exploratory high/dark test procedure [Young et al., Soc. Neurosci. Abs. 14,207 (1988) and Costall et al., Brit. J. Pharmacol. 93,985 (1988)]. Briefly, test compound was administered to a mouse which was placed in a two compartment light-dark activity monitoring box. Control animals typically move to the dark side of the box to avoid the bright light. Animals treated with anxiolytic agents spend more time exploring the lit side of the box than control animals. Results are expressed as percent of total time spent in the lit area, and compared in each case with 10 mg/kg to diazepam.

Anticonvulsant activity was evaluated in two in vivo test procedures which measured the ability of the compounds of the invention to inhibit electrically and chemically induced seizures. Briefly, test compound was administered to adult female mice, followed by either electrical (60 Hz, 5 msec. pulse width 34 nA intensity for 0.2 seconds) or chemical [Metrazole ® (pentylenetetrazol)] challenge. Mice were observed for the occurrence of seizures. Failure of the mice to exhibit a threshold seizure (a single episode of clonic spasm at least 5 seconds in duration) was defined as protection. Results are expressed either as percent protection at a given dose or as the $ED_{50}$ for protection.

The following table summarizes the results of representative compounds of this invention in the inhibition of [$^3$H]-flunitrazepam binding, and inhibition of electrically and chemically induced seizure test procedures.

| Compound | $^3$H-Flu binding* $IC_{50}$ (nM) | MES** Dose (% protection) | SC-MET+ Dose (% protection) |
|---|---|---|---|
| Ex. 1 | 7000 | 100 (0) | 100 (37.5) |
| Ex. 2 | 3100 | 100 (25) | $ED_{50}$ = 48.68 |
| Ex. 3 | 3300 | 100 (0) | 100 (62.5) |
| Ex. 4 | 1600 | +++ | $ED_{50}$ = 38.8 |
| Ex. 5 | 300 | 100 (0) | $ED_{50}$ = 6.92 |
| Ex. 6 | 3900 | 100 (12.5) | $ED_{50}$ = 38.1 |
| Ex. 7 | 7300 | $ED_{50}$ = 76.0 | $ED_{50}$ = 29.4 |
| Ex. 8 | 410 | 31.6 (0) | 31.6 (0) |
| Ex. 9 | 140 | 31.6 (0) | $ED_{50}$ = 15.4 |
| Ex. 10 | 130++ | +++ | $ED_{50}$ = 8.6 |
| Ex. 11 | 390 | 100 (0) | $ED_{50}$ = 16.8 |
| Ex. 12 | 220 | 100 (0) | $ED_{50}$ = 14.8 |

*Inhibition of [$^3$H]-flunitroazepam binding to the benzodiazepine receptor.
**MES = Maximal electroshock test; results given as % protection at a given dose (mg/kg) or $ED_{50}$ (mg/kg).
+SC-MET = subcutaneous Metrazole ® test; results given as % protection at a given dose (mg/kg) or $ED_{50}$ (mg/kg).
++$IC_{50}$ of 160 nM was obtained on re-evaluation.
+++Not evaluated.

The following table summarizes the results of representative compounds of this invention in the light/dark exploratory test procedure for anxiolytic activity. Compounds were compared with diazepam as a reference standard at each dose level.

| | | % of Time in Lit Area | |
|---|---|---|---|
| Compound | Dose (mg/kg) | Compound | Diazepam |
| Example 6 | 3.16 | 36 | 26 |
| | 10.0 | 38 | 26 |
| Example 10 | 0.01 | 35 | 27 |
| | 0.1 | 37 | 27 |
| | 3.16 | 49 | 27 |
| | 5.62 | 49 | 27 |
| | 10.0* | 40 | 26 |
| | 17.8+ | sedation | sedation |
| Example 11 | 1.0 | 38 | 28 |
| | 3.16 | 40 | 28 |
| | 10.0 | 40 | 28 |
| | 31.6 | 53 | 28 |
| Example 12 | 1.0 | 38 | 26 |
| | 3.16 | 40 | 26 |
| | 10.0 | 51 | 26 |
| | 31.6 | 48 | 26 |

*A dose of 10 mg/kg also gave results of 38% for the compounds of Example 10 and 28% for diazepam.
+Doses above 17.8 mg/kg also produced sedation.

Compounds with anticonvulsant activity typically cause ataxia, an undesirable side effect, at some dose. Representative compounds of this invention were evaluated in a loss of righting reflex test procedure [A. P. Roszkowski, J. Pharmacol. Exp. Ther. 129, 75-81 (1960)]. Briefly, the compound to be evaluated was administered to a mouse which was then placed upside down in its cage. Failure to right itself within 20 seconds was considered to be loss of the righting reflex. Results are expressed as percent of mice losing righting reflex at a given dose. The results obtained in this test procedure are summarized in the following table.

| Compound | Dose (mg/kg) | % Loss of Righting Reflex |
|---|---|---|
| Example 1 | 100 | 0 |
| Example 2 | 100 | 0 |
| Example 3 | 100 | 0 |
| Example 4 | 100 | 0 |
| Example 5 | 100 | 0 |
| Example 6 | 100 | 0 |
| Example 7 | 100 | 62.5 |
| Example 8 | 31.6 | 0 |
| Example 9 | + | + |
| Example 10 | 100 | 0 |
| Example 11 | 100 | 0 |
| Example 12 | 100 | 0 |

+Not Evaluated.

The results of these standard pharmacological test procedures demonstrate that the compounds of this invention have anxiolytic and anticonvulsant activity. In addition, the ataxia caused by the compounds of this invention was minimal. By virtue of the results obtained in standard pharmacological tests, the anxiolytic and anticonvulsant agents of this invention are useful in treating anxiety and sleep disorder, causing sedation, and treating seizure disorders, such as epilepsy in mammals.

When the compounds of the invention are employed as anxiolytic or anticonvulsant agents, they can be formulated into oral dosage forms such as tablets, capsules and the like. The compounds can be administered alone or by combining them with conventional carriers, such as magnesium carbonate, magnesium stearate, talc, sugar, lactose, pectin, dextrin, starch, geletin, tragacanth, methylcellulose, sodium carboxymethylcellulose, low melting wax, cocoa butter and the like. Diluents, flavoring agents, solubilizers, lubricants, suspending agents, binders, tablet-disintegrating agents and the like may be employed. The compounds may be encapsulated with or without other carriers. In all cases, the proportion of active ingredients in said compositions both solid and liquid will be at least to impart the desired activity thereto on oral administration. The compounds may also be injected parenterally, in which case they are used in the form of a sterile solution containing other solutes, for example, enough saline or glucose to make the solution isotonic.

The dosage requirements vary with the particular compositions employed, the route of administration, the severity of the symptoms presented and the particular subject being treated. Treatment will generally be initiated with small dosage less than the optimum dose of the compound. Thereafter the dosage is increased until the optimum effect under the circumstances is reached. Based on the results of the standard pharmacologic test procedures, projected daily dosages of active compound would be 0.5–60 mg/kg for use as an anxiolytic and 1–100 mg/kg for use as an anticonvulsant. In general, the compounds of the invention are most desirably administered at a concentration that will generally afford effective results without causing any harmful or deleterious side effects and can be administered either as a single unit dose, or if desired, the dosage may be divided into convenient subunits administered at suitable times throughout the day.

The following examples show the preparation of representative compounds of this invention.

EXAMPLE 1

2-(4-Chlorophenyl)-3-(2-pyridinylmethyl)-3H-imidazo[4,5-b]pyridine

To a stirred solution of 2-chloro-3-nitropyridine (26.56 g, 0.168 mol) in absolute ethanol (250 mL) was added 2-(aminomethyl)pyridine (20.0 g, 0.185 mol) and triethylamine (16.99 g, 0.168 mol). The solution was heated at reflux for 2 hr and evaporated under reduced pressure. The residue was triturated in ethyl acetate several times and filtered. The filtrate was washed 3 times with a saturated sodium chloride solution, dried (sodium sulfate), filtered and evaporated under reduced pressure to give 36.8 g of N-(3-nitro-2-pyridinyl)-2-pyridinemethanamine (95% yield). A 1.0 g portion of the solid was recrystallized from isopropyl ether and dried under high vacuum to give 0.57 g of N-(3-nitro-2-pyridinyl)-2-pyridinemethanamine, mp 112°–115° C.

Anal. for $C_{11}H_{10}N_4O_2$: Calcd: C, 57.39; H, 4.38; N, 24.34. Found: C, 57.25; H, 4.33; N, 24.29.

A solution of N-(3-nitro-2-pyridinyl)-2-pyridinemethanamine, prepared in the previous paragraph (35.6 g, 0.155 mol) was hydrogenated in tetrahydrofuran (500 mL) over 5% palladium/charcoal at 40° C. When 87% of the theoretical amount of hydrogen was absorbed, the mixture was filtered. Triethylamine (8.45 g, 0.0837 mol) and 4-chlorobenzoyl chloride (14.65 g, 0.0837 mol) were added simultaneously and dropwise to 45% of this solution. The mixture was stirred at room temperature overnight and the solvents were removed under reduced pressure. The residue was partitioned between ethyl acetate and water and the insoluble solid 4-chloro-N-[2-[(2-pyridinylmethyl)amino]-3-pyridinyl]benzamide was collected by filtration (14.65 g, 62% yield). The layers of the filtrate were separated. The organic layer was washed once with a 5% potassium hydroxide solution and once with a saturated sodium chloride solution. The organic layer was dried (magnesium sulfate), treated with charcoal, filtered and evaporated under reduced pressure. A little ethyl acetate was added to give a solid which was collected by filtration and recrystallized from ethyl acetate/isopropyl ether and dried under high vacuum at 50° C. to give 1.22 g, mp 198°–201° C.

Anal. for $C_{18}H_{15}N_4OCl$: Calcd: C, 63.81; H, 4.46; N, 16.54. Found: C, 63.72; H, 4.44; N, 16.45.

A solution of 4-chloro-N-[2-[(2-pyridinylmethyl)amino]-3-pyridinyl]benzamide (14.65 g, 0.0433 mol) prepared in the previous paragraph and ethylene glycol (145 mL) were heated at reflux for 1.5 hr and then stirred at room temperature overnight. The resulting solid was collected by filtration, rinsed several times with water, recrystallized from isopropanol/water and dried under high vacuum at 70° C. to give 10.36 g (74% yield) of the title compound, mp 144°–146° C.

Anal. for $C_{18}H_{13}N_4Cl$: Calcd: C, 67.40; H, 4.08; N, 17.46. Found: C, 67.28; H, 3.97; N, 17.40.

EXAMPLE 2

2-(4-Methylphenyl)-3-(2-pyridinylmethyl)-3H-imidazo[4,5-b]pyridine

The title compound was prepared by the method of the preceding Example except that the hydrogenation product was acylated with p-toluoyl chloride. The product was isolated as a hemihydrate.

Anal. for $C_{19}H_{17}N_4O_{0.5}$: Calcd: C, 73.77; H, 5.54; N, 18.11. Found: C, 74.22; H, 5.29; N, 18.19.

EXAMPLE 3

5-Chloro-2-(4-chlorophenyl)-3-(2-pyridinylmethyl)-3H-imidazo[4,5-b]pyridine

The title compound was prepared using the method described in Example 1 by reacting 2,6-dichloro-3-nitropyridine with 2-(aminomethyl)pyridine to give N-6-chloro-3-nitro-2-pyridinyl)-2-pyridinemethanamine which was hydrogenated over platinum/carbon and acylated with 4-chlorobenzoyl chloride. Ring closure to give the title compound was accomplished as described in Example 1.

Anal. for $C_{18}H_{12}N_4Cl_2$: Calcd: C, 60.86; H, 3.40; N, 15.77. Found: C, 60.56; H, 3.34; N, 15.67.

EXAMPLE 4

5-Chloro-2-(4-methylphenyl)-3-(2-pyridinylmethyl)-3H-imidazo[4,5-b]pyridine

The title compound was prepared using the method described in Example 1 by reacting 2,6-dichloro-3-nitropyridine with 2-(aminomethyl)pyridine to give N-(6-chloro-3-nitro-2-pyridinyl)-2-pyridinemethanamine which was hydrogenated over platinum/carbon and acylated with 4-toluoyl chloride. Ring closure to give the title compound was accomplished as described in Example 1.

Anal. for $C_{19}H_{15}N_4Cl$: Calcd: C, 68.16; H, 4.52; N, 16.73. Found: C, 68.15; H, 4.39; N, 16.74.

EXAMPLE 5

5-Chloro-3-(1H-imidazol-2-ylmethyl)-2-(4-methylphenyl)-3H-imidazo[4,5-b]pyridine The title compound was prepared by the method described in Example 1 by reacting 2,6-dichloro-3-nitropyridine with 1H-imidazol-2-methanamine hydrochloride to give N-[6-chloro-2-[(1H-imidazol-2-ylmethyl)amino]-3-pyridinyl]-4-methylbenzamide which was hydrogenated and acylated with 4-toluoyl chloride. Ring closure to give the title compound was accomplished with methanesulfonic acid in 2-methoxyethanol.

Anal. for $C_{17}H_{14}N_5Cl$: Calcd: C, 63.06; H, 4.36; N, 21.63. Found: C, 62.93; H, 4.31; N, 21.47.

EXAMPLE 6

5-Methyl-2-(4-methylphenyl)-3-(2-pyridinylmethyl)-3H-imidazo[4,5-b]pyridine

The title compound was prepared by the method described in Example 1 except that the hydrogenation/acylation step was performed first. Thus, 2-chloro-3-nitro-6-methylpyridine was hydrogenated and acylated with 4-toluoyl chloride using the procedure described in Example 1. The intermediate N-(2-chloro-6-methyl-3-pyridinyl)-4-methyl-benzamide was isolated and reacted with 2-(aminomethyl)pyridine as described in Example 1, except that excess 2-(aminomethyl)pyridine was used instead of triethylamine. Ring closure to give the title compound was accomplished by refluxing the above described reaction mixture.

Anal. for $C_{20}H_{18}N_4$: Calcd: C, 76.41; H, 5.77; N, 17.82. Found: C, 76.34; H, 5.69; N, 17.83.

EXAMPLE 7

2-(4-Chlorophenyl)-5-methyl-3-(2-pyridinylmethyl)-3H-imidazo[4,5-b]pyridine

The title compound was prepared by using the method described in Example 6, except that 4-chlorobenzoyl chloride was used as the acylating agent instead of 4-toluoyl chloride.

Anal. for $C_{19}H_{15}N_4Cl$: Calcd: C, 68.16; H, 4.52; N, 16.73. Found: C, 67.99; H, 4.32; N, 16.67.

EXAMPLE 8

2-(4-Chlorophenyl)-3-(1H-imidazol-2-ylmethyl)-3H-imidazo[4,5-b]pyridine

A suspension of 2-chloro-3-nitropyridine (7.74 g, 0.0490 mol) and 2-aminomethyl imidazole dihydrochloride (10.0 g, 0.0588 mol) in absolute ethanol (250 mL) was stirred at room temperature and triethylamine (11.88 g, 0.118 mol) was added. The mixture was heated at reflux for 4 hours, additional triethylamine (5.9 g, 0.0588 mol) was added, and refluxing was continued for 2 additional hours. The solvents were removed under reduced pressure, and the residue was partitioned between ethyl acetate and water. The insoluble solid was collected by filtration and was combined with the product that was obtained by separating the layers of the filtrate followed by washing the ethyl acetate with saturated sodium chloride solution. The product was recrystallized from ethyl acetate/isopropyl ether/light petroleum ether to give 3.10 g of crude N-(1H-imidazol-2-ylmethyl)-3-nitro-2-pyridine. An additional recrystallization of 0.5 g of the solid from ethyl acetate/light petroleum ether gave 0.33 g, mp 144°–146° C.

Anal. for $C_9H_9N_5O_2$: Calcd: C, 49.31; H, 4.14; N, 31.95. Found: C, 49.36; H, 4.05; N, 31.88.

A solution of N-(1H-imidazol-2-ylmethyl)-3-nitro-2-pyridinamine (6.8 g, 0.3105 mol) in tetrahydrofuran (200 mL) was hydrogenated over 5% palladium-on-carbon (0.68 g) at 40° C. The mixture was cooled to room temperature and filtered through celite. The filter cake was rinsed with methanol, and the combined filtrates were evaporated under reduced pressure to give 5.3 g of the amine. The amine was refluxed in tetrahydrofuran (300 mL) and triethylamine (5.63 g, 0.0558 mol) was added. The mixture was cooled slightly and 4-chlorobenzoyl chloride (5.37 g, 0.0307 mol) was added. The mixture was heated at reflux for 30 minutes and then stirred at room temperature overnight. The solvents were removed under reduced pressure, and the residue was partitioned between ethyl acetate and water. The aqueous layer was extracted again with ethyl acetate, and the combined organic layers were washed once with saturated sodium chloride solution, dried (sodium sulfate), filtered, and evaporated under reduced pressure to give 10.8 g of a mixture of products. A 9.2 g portion of this product was heated in warm ethyl acetate, and the insoluble solid was collected by filtration. This solid was recrystallized from a larger amount of ethyl acetate and was combined with pure title compound that was obtained by column chromatography (200 g of silica gel, ethyl acetate) of the filtrate followed by evaporation of solvent (2.1 g). The combined products were recrystallized from ethyl acetate/light petroleum ether and dried under high vacuum at 60° C. to give 2.03 g of the title compound, mp 184°–185° C.

Anal. for $C_{16}H_{12}N_5Cl$: Calcd: C, 62.04; H, 3.90; N, 22.61. Found: C, 61.83; H, 3.77; N, 22.45.

EXAMPLE 9

3-(1H-Imidazol-2-ylmethyl)-2-(4-methylphenyl)-3H-imidazo[4,5-b]pyridine

The title compound was prepared by using the method described in Example 8 except that 4-toluoyl chloride was used in the acylation step instead of 4-chlorobenzoyl chloride and ring closure to obtain the title compound was done at reflux in toluene using a Dean-Starke trap to remove water.

Anal. for $C_{17}H_{15}N_5$: Calcd: C, 70.57; H, 5.22; N, 24.20. Found: C, 70.47; H, 5.11; N, 24.07.

EXAMPLE 10

5-Chloro-2-(4-chlorophenyl)-3-(1H-imidazol-2-ylmethyl)-3H-imidazo[4,5-b]pyridine The title compound was prepared by using the method described in Example 8 except that 2,6-dichloro-3-nitropyridine was used instead of 2-chloro-3-nitropyridine and the ring closure to obtain the title compound was done at reflux in toluene using a Dean-Starke trap to remove water.

Anal. for $C_{16}H_{11}N_5Cl_2$: Calcd: C, 55.83; H, 3.22; N, 20.35. Found: C, 55.66; H, 3.14; N, 20.08.

EXAMPLE 11

2-(4-Chlorophenyl)-3-(4-methyl-1H-imidazol-2-ylmethyl)-3H-imidazo[4,5-b]pyridine A solution of 2-chloro-3-nitropyridine (23.52 g, 0.149 mol), 4-methyl-1H-imidazol-2-methanamine hydrochloride (containing 2 moles of ammonium chloride, 46.0 g, 0.160 mol), and triethylamine (37.6 g, 0.372 mol) in absolute ethanol was refluxed under nitrogen for 5 hours and filtered while hot. The solution was evaporated under reduced pressure, water was added, and the product was extracted with 2 portions of ethyl acetate. The solid in the ethyl acetate layers was collected by filtration and combined with the solid obtained from concentration of the ethyl acetate layer. The combined solids (23.8 g) were recrystallized from hot ethyl acetate to give 5.20 g of solid. A solid, which had precipitated from the above aqueous washings, was collected by filtration and combined with the evaporated mother liquor (ethyl acetate) and heated in ethyl acetate. A filtration while hot gave 4.12 g of solid, which was combined with the 5.20 g of solid from above, to give a solid of which 9.4 g was hydrogenated in 1:1 tetrahydrofuran/methanol (200 mL) over 5% palladium/carbon (0.15 g) at 50° C. for 2 days. The reaction mixture was filtered and evaporated under reduced pressure. To 45% of the residue (0.0181 mol of reduced amine) dissolved in tetrahydrofuran (150 mL) was added triethylamine (2.75 g, 0.0272 mol) and 4-chlorobenzoyl chloride (4.76 g, 0.0272 mol). The mixture was refluxed for several hours, cooled to room temperature and evaporated under reduced pressure. Water was added and the product was extracted 2 times with ethyl acetate. The combined organic layers were washed 3 times with water, twice with a saturated sodium bicarbonate solution and once with a saturated sodium chloride solution. The organic layer was dried (magnesium sulfate), treated with charcoal, filtered, and evaporated to give 5.3 g of solid. To ethanol (100 mL) and potassium hydroxide (1.12 g) in water (100 mL) 4.1 g of the solid was added. The mixture was refluxed for 2 hr and acidified with a 3N hydrochloride acid solution. Upon stirring at room temperature, a solid precipitated which was removed by filtration. The filtrate was evaporated under reduced pressure until only an aqueous solution was left and then basified with sodium bicarbonate. The product was extracted 3 times with ethyl acetate. The combined organic extracts were washed twice with a saturated sodium bicarbonate solution and once with a saturated sodium chloride solution, dried (sodium sulfate), filtered, and evaporated under reduced pressure to give 2.4 g of solid. The solid was eluted through 50 g of silica gel (ethyl acetate) to give a fraction which was evaporated, recrystallized from ethyl acetate/isopropyl ether, and dried under high vacuum at 50° C. to give 0.45 g of the title compound, mp 192°–195° C.

Anal. for $C_{17}H_{14}N_5Cl$: Calcd: C, 63.06; H, 4.36; N, 21.63. Found: C, 62.89; H, 4.26; N, 21.35.

EXAMPLE 12

2-(4-Methyl-1H-imidazol-2-ylmethyl)-2-(4-methylphenyl)-3H-imidazo[4,5-b]pyridine The title compound was prepared by the method described in Example 11 except that 4-toluoyl chloride was used in the acylation step instead of 4-chlorobenzoyl chloride.

Anal. for $C_{18}H_{17}N_5$: Calcd: C, 71.27; H, 5.65; N, 23.08. Found: C, 71.16; H, 5.53; N, 22.81.

What is claimed is:

1. A compound having the formula

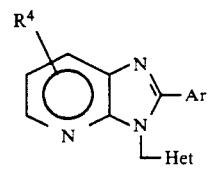

wherein
Ar is

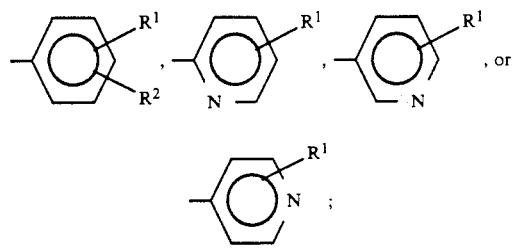

Het is

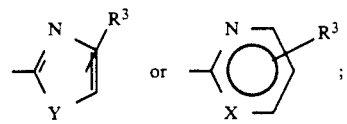

$R^1$, $R^2$, and $R^3$ are each, independently, hydrogen, alkyl of 1–6 carbon atoms, aralkyl of 7–10 carbon atoms, alkoxy of 1–6 carbon atoms, carbalkoxy of 2–7 carbon atoms, trifluoromethyl, halo, cyano, or nitro;

$R^4$ is hydrogen, alkyl of 1–6 carbon atoms, aralkyl of 7–10 carbon atoms, alkoxy of 1–6 carbon atoms, carbalkoxy of 2–7 carbon atoms, halo, or trifluoromethyl;

Y is NH, O, or S;

X is CH, or N;

or a pharmaceutically acceptable salt thereof.

2. A compound of claim 1 of the formula

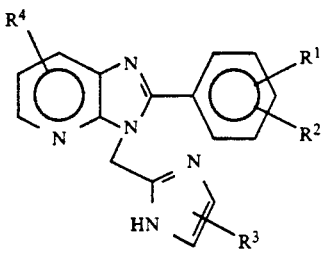

or a pharmaceutically acceptable salt thereof.

3. A compound of claim 1 of the formula

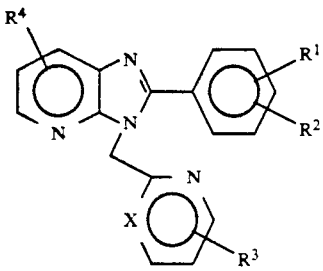

or a pharmaceutically acceptable salt thereof.

4. A compound of claim 1 which is 2-(4-chlorophenyl)-3-(2-pyridinylmethyl)-3H-imidazo[4,5-b]pyridine or a pharmaceutically acceptable salt thereof.

5. A compound of claim 1 which is 2-(4-methylphenyl)-3-(2-pyridinylmethyl)-3H-imidazo[4,5-b]pyridine or a pharmaceutically acceptable salt thereof.

6. A compound of claim 1 which is 5-chloro-2-(4-chlorophenyl)-3-(2-pyridinylmethyl)-3H-imidazo[4,5-b]pyridine or a pharmaceutically acceptable salt thereof.

7. A compound of claim 1 which is 5-chloro-2-(4-methylphenyl)-3-(2-pyridinylmethyl)-3H-imidazo[4,5-b]pyridine or a pharmaceutically acceptable salt thereof.

8. A compound of claim 1 which is 5-chloro-3-(1H-imidazol-2-ylmethyl)-2-(4-methylphenyl)-3H-imidazo[4,5-b]pyridine or a pharmaceutically acceptable salt thereof.

9. A compound of claim 1 which is 5-methyl-2-(4-methylphenyl)-3-(2-pyridinylmethyl)-3H-imidazo[4,5-b]pyridine or a pharmaceutically acceptable salt thereof.

10. A compound of claim 1 which is 2-(4-chlorophenyl)-5-methyl-3-(2-pyridinylmethyl)-3H-imidazo[4,5-b]pyridine or a pharmaceutically acceptable salt thereof.

11. A compound of claim 1 which is 2-(4-chlorophenyl)-3-(1H-imidazol-2-ylmethyl)-3H-imidazo[4,5-b]pyridine or a pharmaceutically acceptable salt thereof.

12. A compound of claim 1 which is 3-(1H-imidazol-2-ylmethyl)-2-(4-methylphenyl)-3H-imidazo[4,5-b]pyridine or a pharmaceutically acceptable salt thereof.

13. A compound of claim 1 which is 5-chloro-2-(4-chlorophenyl)-3-(1H-imidazol-2-ylmethyl)-3H-imidazo[4,5-b]pyridine or a pharmaceutically acceptable salt thereof.

14. A compound of claim 1 which is 2-(4-chlorophenyl)-3-(4-methyl-1H-imidazol-2-ylmethyl)-3H-imidazo[4,5-b]pyridine or a pharmaceutically acceptable salt thereof.

15. A compound of claim 1 which is 3-(4-methyl-1H-imidazol-2-ylmethyl)-2-(4-methylphenyl)-3H-imidazo[4,5-b]pyridine or a pharmaceutically acceptable salt thereof.

16. A method of treating anxiety, causing sedation, or inducing sleep in mammals in need of such treatment by administering an effective amount of a compound having the formula

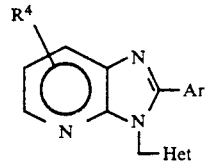

wherein
Ar is

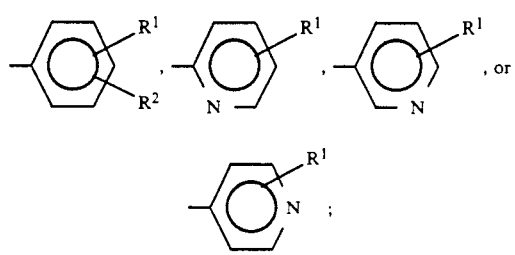

Het is

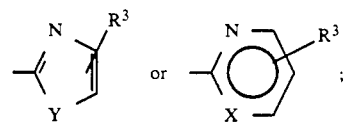

R¹, R², and R³ are each, independently, hydrogen, alkyl of 1-6 carbon atoms, aralkyl of 7-10 carbon atoms, alkoxy of 1-6 carbon atoms, carbalkoxy of 2-7 carbon atoms, trifluoromethyl, halo, cyano, or nito;

R⁴ is hydrogen, alkyl of 1-6 carbon atoms, aralkyl of 7-10 carbon atoms, alkoxy of 1-6 carbon atoms, carbalkoxy of 2-7 carbon atoms, halo, or trifluoromethyl;

Y is NH, O, or S;

X is CH, or N;

or a pharmaceutically acceptable salt thereof.

17. A method of treating seizure disorders in mammals in need of such treatment by administering an effective amount of a compound having the formula

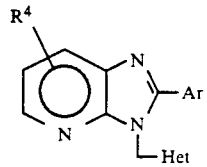

wherein
Ar is

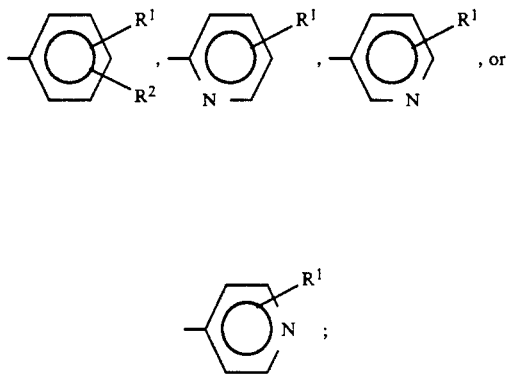

Het is

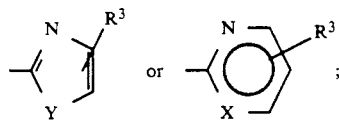

$R^1$, $R^2$, and $R^3$ are each, independently, hydrogen, alkyl of 1-6 carbon atoms, aralkyl of 7-10 carbon atoms, alkoxy of 1-6 carbon atoms, carbalkoxy of 2-7 carbon atoms, trifluoromethyl, halo, cyano, or nitro;

$R^4$ is hydrogen, alkyl of 1-6 carbon atoms, aralkyl of 7-10 carbon atoms, alkoxy of 1-6 carbon atoms, carbalkoxy of 2-7 carbon atoms, halo, or trifluoromethyl;

Y is NH, O, or S;

X is CH, or N;

or a pharmaceutically acceptable salt thereof.

18. A pharmaceutical composition comprising a compound of claim 1 or a pharmaceutically acceptable salt thereof and a pharmaceutically acceptable carrier.

19. A composition as claimed in claim 18, in unit dosage form.

* * * * *